(12) United States Patent
Young et al.

(10) Patent No.: US 7,968,859 B2
(45) Date of Patent: Jun. 28, 2011

(54) WAFER EDGE DEFECT INSPECTION USING CAPTURED IMAGE ANALYSIS

(75) Inventors: Roger Y. B. Young, Vancouver, WA (US); John A. Knoch, Portland, OR (US); Jason W. McNichols, Portland, OR (US)

(73) Assignee: LSI Corporation, Milpitas, CA (US)

( * ) Notice: Subject to any disclaimer, the term of this patent is extended or adjusted under 35 U.S.C. 154(b) by 2035 days.

(21) Appl. No.: 10/628,614

(22) Filed: Jul. 28, 2003

(65) Prior Publication Data
US 2005/0023491 A1 Feb. 3, 2005

(51) Int. Cl.
*G01N 21/86* (2006.01)
(52) U.S. Cl. .................................. 250/559.4; 250/221
(58) Field of Classification Search .................. 250/221, 250/559.3, 548, 559.4, 310, 307, 306; 356/237.1–237.5, 614; 382/141–145
See application file for complete search history.

(56) References Cited

U.S. PATENT DOCUMENTS

| | | | |
|---|---|---|---|
| 6,062,084 A | 5/2000 | Chang et al. | |
| 6,432,800 B2 * | 8/2002 | Park | 438/582 |
| 6,545,752 B1 | 4/2003 | Swan et al. | |
| 6,566,673 B1 | 5/2003 | Swan et al. | |
| 6,906,794 B2 * | 6/2005 | Tsuji | 356/237.4 |

* cited by examiner

*Primary Examiner* — Que T Le
(74) *Attorney, Agent, or Firm* — Otterstedt, Ellenbogen & Kammer, LLP

(57) ABSTRACT

A wafer edge defect inspection method and apparatus for use in an integrated circuit fabrication system includes an image capturing device for capturing images of the edges of wafers, a database in which the images are stored and accessible for analysis and a computer for analyzing the images of one or more wafer edges to locate edge defects and for evaluating the performance of the fabrication system. The inspection and data storage are performed automatically. The database storage enables detailed analysis of many wafers and fabrication process steps.

10 Claims, 4 Drawing Sheets

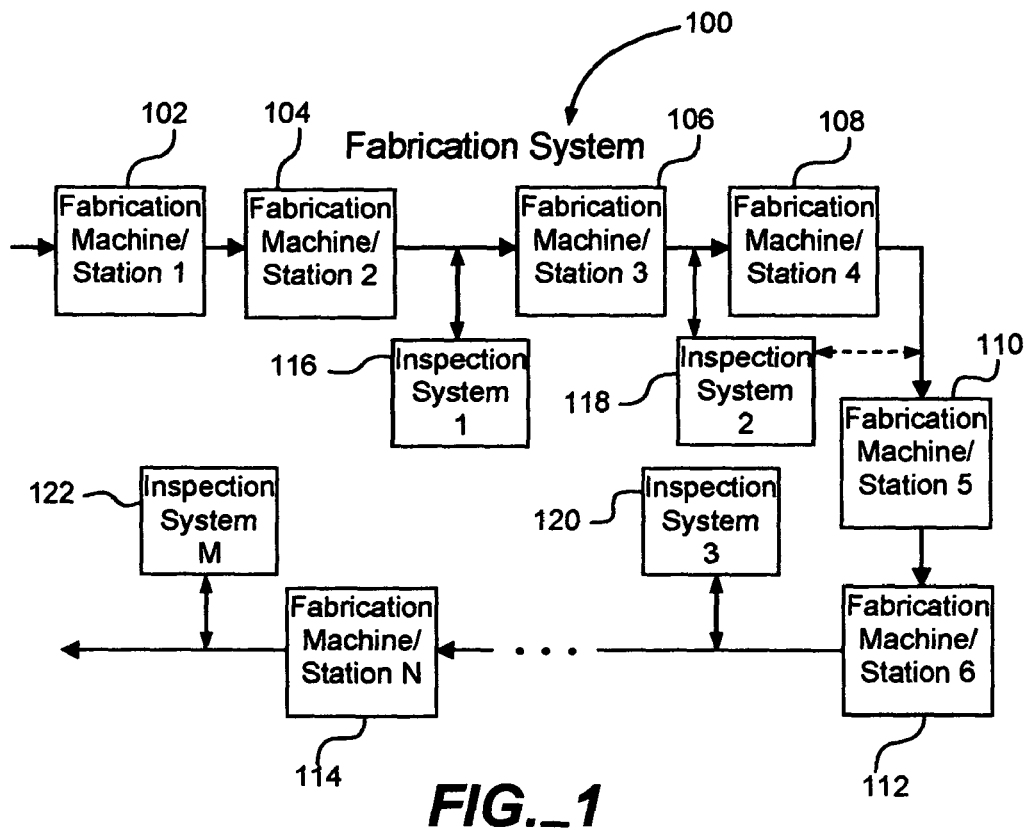
FIG._1
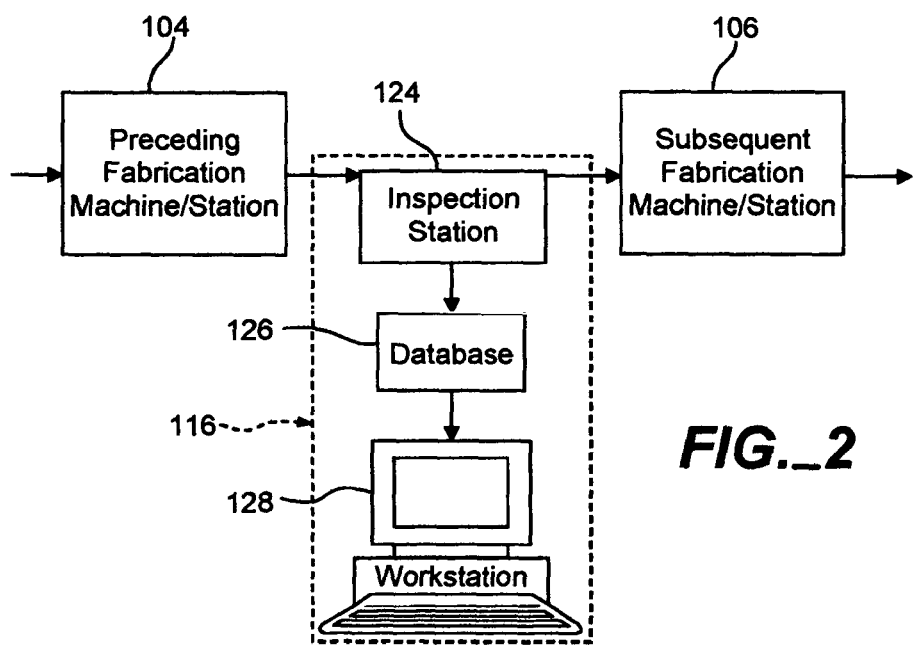
FIG._2

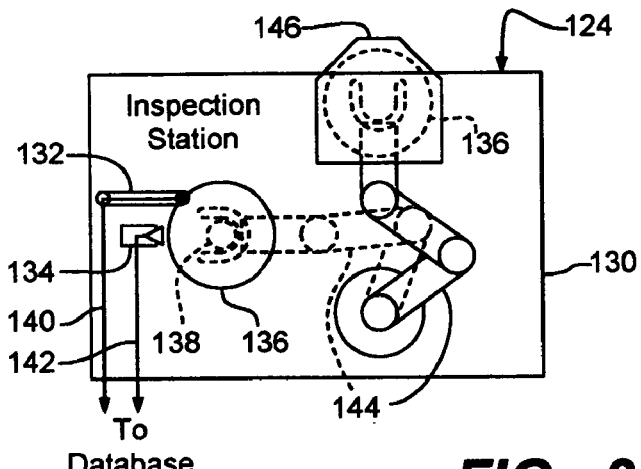
FIG._3
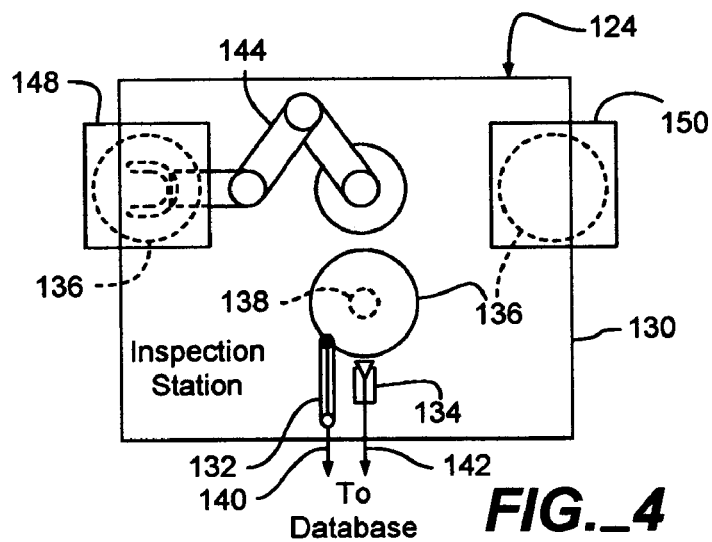
FIG._4
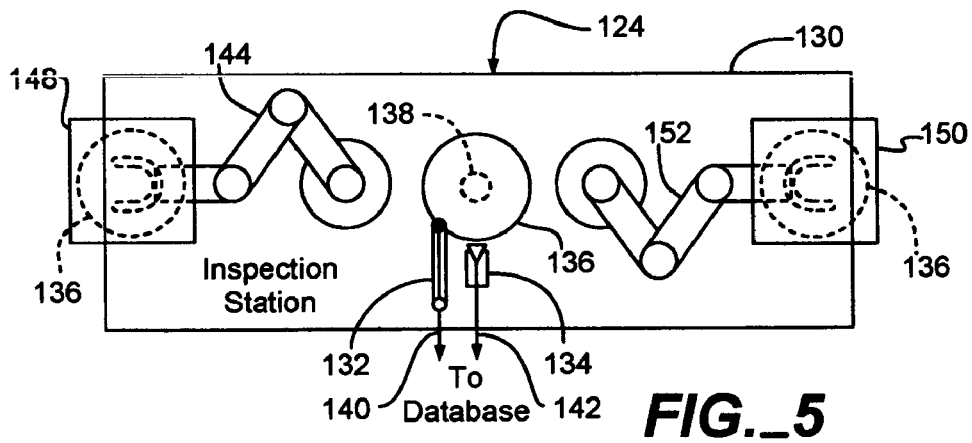
FIG._5

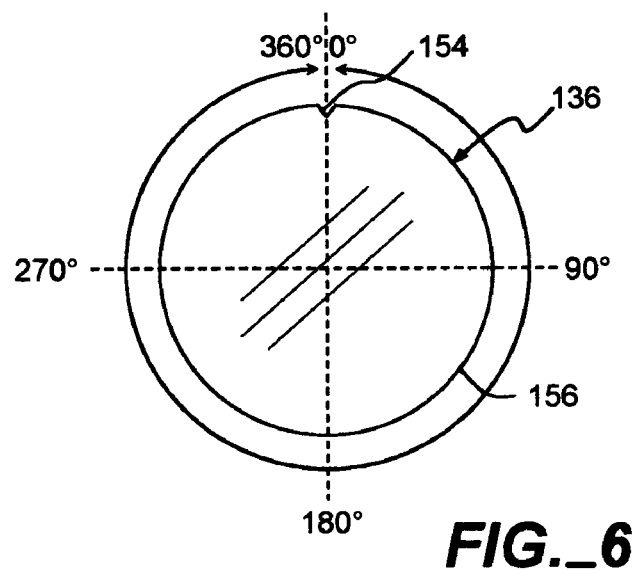
FIG._6
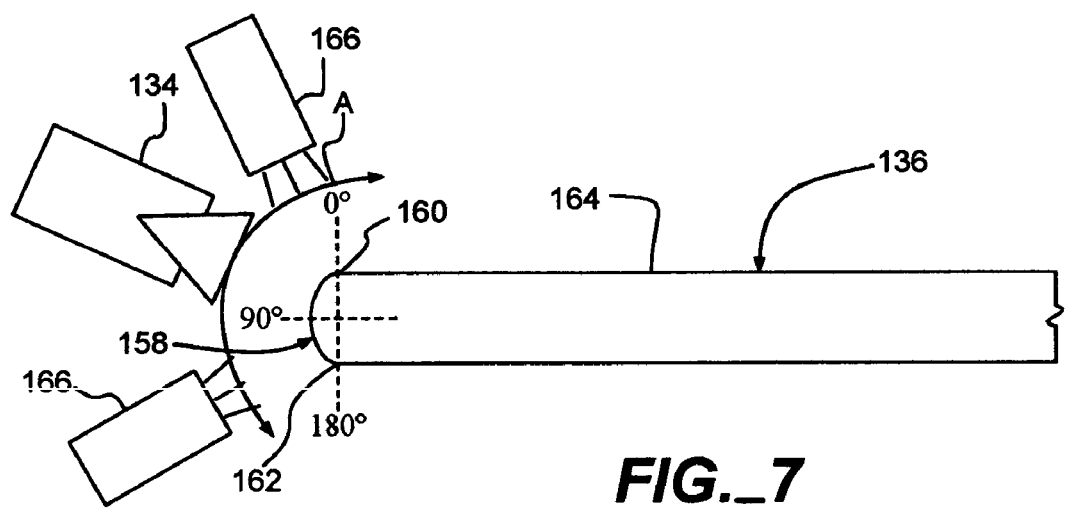
FIG._7

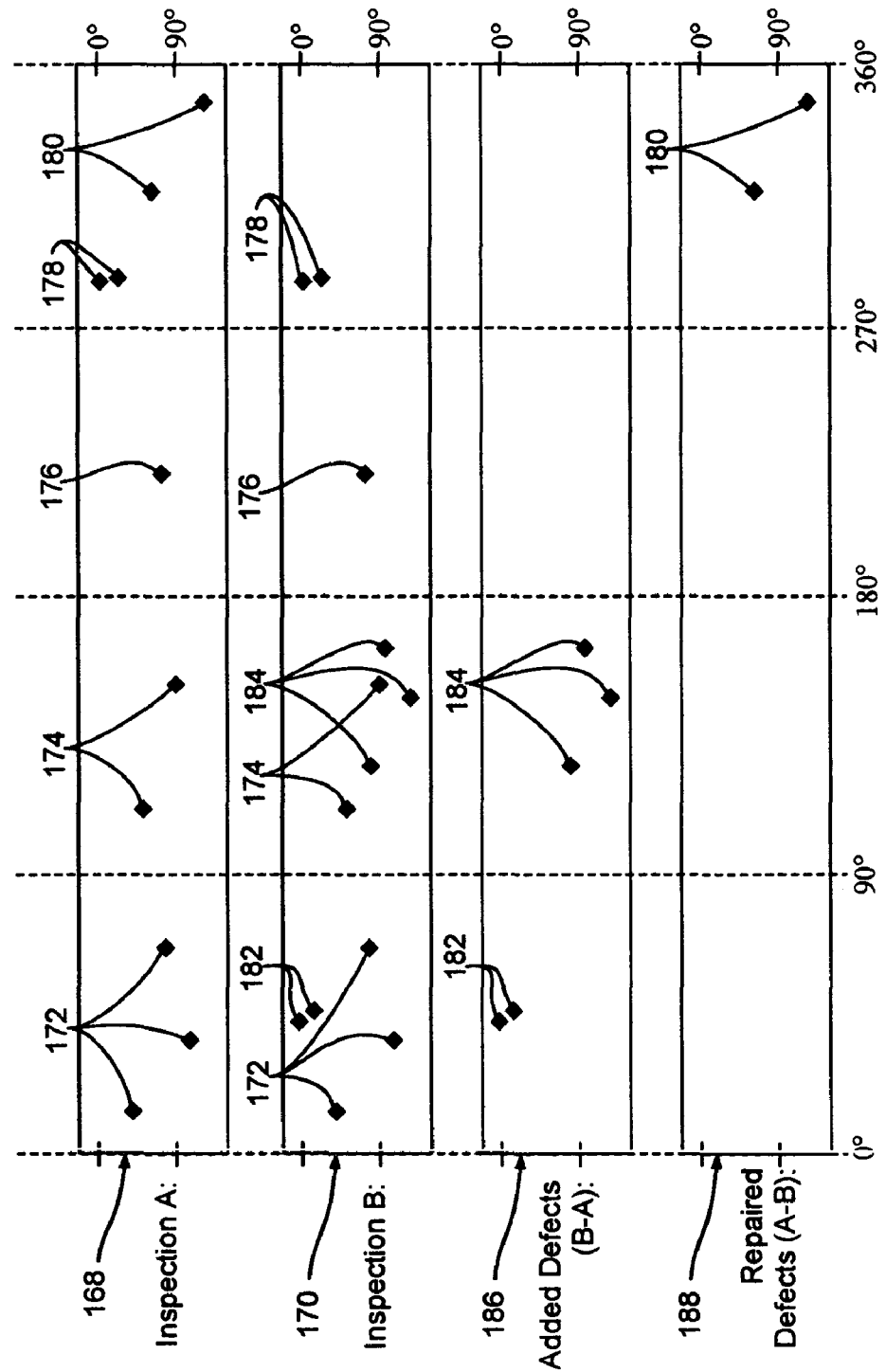
FIG._8

WAFER EDGE DEFECT INSPECTION USING CAPTURED IMAGE ANALYSIS

FIELD OF THE INVENTION

This invention relates to wafer defect inspection within fabrication systems that form integrated circuits (ICs) on semiconductor wafers. In particular, this invention relates to new and improved techniques for inspecting the edges of the wafers for defects preferably between various process steps during the over-all fabrication of the wafers within the fabrication system.

BACKGROUND OF THE INVENTION

A significant trend throughout IC development has been to try to increase the "yield rate" of semiconductor fabrication systems. The yield rate refers to the percentage of usable IC's produced by a fabrication system compared to the total number attempted. Similarly, the yield rate may refer to the percentage of usable IC's obtained from an average semiconductor wafer that is processed through the fabrication system. A semiconductor wafer is essentially a thin disc of highly purified semiconductor material on which many IC's are fabricated together and then separated for individual packaging.

Significant factors that can negatively impact the yield rate are the number and size of defects in the wafer. Defects may include cracks, crazes (i.e. microscopic cracks), chips, flakes, scratches, marks, missing/broken edges and particle and residue contamination, among others. Defects are particularly detrimental to the yield rate when they occur on the top surface of the wafer, since the top surface is the region where the IC's are formed on the wafer. Of historically lesser concern have been any other areas of the wafer, such as the bottom surface and the edge, or bevel, of the wafer. Since these areas are further from the formation of the IC's, any defects therein have been considered to have less of an impact on the yield rate for the IC's. Thus, many wafer-inspection and defect-detection techniques have been developed to inspect for defects in the top surface of wafers; whereas, comparatively few techniques have been developed to inspect for defects elsewhere on the wafers.

Until recently, wafer edge inspection has primarily been performed by manual visual inspection by a worker in the fabrication plant. A high-resolution camera may be used to generate an image of the wafer edge on a monitor, which the worker manually views for defects. This edge inspection technique is in stark contrast to the various complex computerized image-analysis techniques, among other inspection techniques, that have been developed to inspect the top surface of the wafers. Recent developments in non-visual inspection of wafer edges have merely included emitter/detector pairs for ultrasonic waves and laser/light beams for limited detection of cracks and breaks at the edge. These techniques may be used in combination with visual inspection to confirm the presence of any defects in the wafer edge. Detailed image-analysis techniques have not been used for wafer edge defect detection, since it has been commonly considered unnecessary to do so.

Additionally, current non-visual wafer edge inspection techniques may record data plots (not images), which a worker may review for indications of defects or a computer may analyze for possible defects. Though the data may be stored for a time, the purpose of the data is generally for immediate pass/fail analysis of the wafer, so the wafer may be passed on for further processing, discarded as unusable or rerouted for rework or repair.

It is with respect to these and other considerations that the present invention has evolved.

SUMMARY OF THE INVENTION

The present invention arose out of the recognition of the importance of wafer edge defects relative to yield rate and the need to give greater consideration to edge defects during wafer fabrication. It was realized that defects at the edge of a wafer, though they are far from the IC's on the surface of the wafer, frequently cause problems in the fabrication of the IC's. For instance, process-induced edge contamination and flaking from the wafer edge are types of defects that can cause considerable problems in IC fabrication, particularly when particles or flakes break off of the edge and land on the top surface of the wafer during a process step. Additionally, cracks in the wafer edge may propagate to the interior of the wafer, particularly during process steps that thermally cycle the wafer. Furthermore, with the introduction of new wafer processing technologies such as the use of low-K dielectrics and copper dual damascene processes, new and more pronounced edge related defect mechanisms, or causes, (e.g. film separation during thermal processing, stress induced de-lamination, changes to film properties during subsequent process steps, etc.) have occurred. Therefore, there is a need for wafer edge inspection that goes beyond the limited capabilities of the visual inspection techniques and emitter/detector pair techniques described above.

Visual inspection of the edges has proven to be too time-consuming and unreliable to adequately address the problem of wafer edge defects during the over-all fabrication process. Additionally, the emitter/detector pair techniques detect too limited of a range of types of defects. For instance, the process-induced edge contamination and the flaking from the wafer edge are types of defects that the emitter/detector pair techniques cannot detect.

Furthermore, it was realized that a system of storing and managing inspection data for future analysis is necessary to perform a detailed investigation of the efficiency of the over-all fabrication system in order to optimize each process step within the fabrication system and maximize the yield rate. The inspection techniques heretofore developed do not include such a feature.

According to various embodiments, therefore, the present invention preferably involves methods and apparatus for automatic image-capture, image-data-storage and image-analysis using a database within which the image data is stored and managed. The image data is preferably accessible for comparison and analysis of wafers at different points in the fabrication system so that the effects of a given process step on the addition or repair of edge defects can be determined. Additionally, the image data is preferably accessible for comparison and analysis of different wafers at the same point in the fabrication system so that the effects of changing a given process step can be determined.

According to certain embodiments, the present invention preferably includes an image capturing device, such as a scanning electron microscope or an optical review system (e.g. a camera, etc.). The image capturing device sends wafer edge images to the database. Preferably more than one image capturing device (or an inspection station within which the image capturing device is incorporated) is located within the fabrication system relative to selected fabrication stations within which particular process steps are performed. Using a workstation, or computer, a user preferably accesses the wafer edge images and instructs the computer to perform a variety of analyses on one or more images at a time to discover the effects of various process steps in the fabrication system.

A more complete appreciation of the present invention and its scope, and the manner in which it achieves the above noted improvements, can be obtained by reference to the following detailed description of presently preferred embodiments of the invention taken in connection with the accompanying drawings, which are briefly summarized below, and the appended claims.

BRIEF DESCRIPTION OF THE DRAWINGS

FIG. 1 is a simplified schematic of a fabrication system having inspection stations and in which the present invention is incorporated.

FIG. 2 is a simplified schematic of an enlargement of a portion of the fabrication system, including the inspection stations, shown in FIG. 1.

FIGS. 3, 4 and 5 are simplified plan views of alternative embodiments for the inspection stations shown in FIGS. 1 and 2.

FIG. 6 is a simplified plan view of a semiconductor wafer to be processed by the fabrication system shown in FIG. 1 and inspected by one or more of the inspection stations shown in FIGS. 1-5.

FIG. 7 is a simplified elevation view of the wafer shown in FIG. 6 and an image capturing device incorporated in the inspection stations shown in FIGS. 1-5.

FIG. 8 is exemplary inspection result graphs of defects on an edge of the wafer shown in FIGS. 6 and 7

DETAILED DESCRIPTION

An exemplary fabrication system 100 that fabricates integrated circuits (IC's) (not shown) on semiconductor wafers (not shown) is shown in FIG. 1. The fabrication system 100 includes several conventional fabrication machines, or stations, 102-114, such as metal deposition devices, ion implantation devices, epitaxial growth chambers, ovens, spin-on-glass devices, etc. Thus, the fabrication stations 102-114 perform various conventional process steps in a specific processing order on the wafers in order to fabricate the IC's. The fabrication system 100 also includes inspection systems 116-122. Each inspection system 116-122 is interposed between two fabrication stations 102-114 to intercept one or more or all of the wafers passing between the fabrication stations 102-114 for inspection purposes. Each inspection system 116, 118, 120 and 122 corresponds to the fabrication station 104, 106, 112 and 114, respectively, that immediately precedes it in the processing order. The inspection systems 116-122, thus, inspect the wafers within the fabrication system 100 after specific processing steps have been performed in the corresponding fabrication stations 104, 106, 112 and 114. The inspection systems 116-122 inspect and analyze the wafers for defects in the edges thereof at selected points in the fabrication system 100 using image-capture and image-analysis. The inspection systems 116-122 may also categorize the type of each wafer edge defect detected through the inspection and analysis. Exemplary types of wafer edge defects that can be detected by the inspection systems 116-122 include cracks crazes (i.e. microscopic cracks), chips, flakes, scratches, marks, missing/broken edges and particle and residue contamination, among others.

The inspection systems 116-122 are preferably located within the fabrication system 100 to enable a user or operator of the fabrication system 100 to evaluate the performance of the fabrication system 100 at selected points therein with respect to wafer edge defects. The information obtained further enables the user to evaluate the performance of individual fabrication stations (e.g. 106) by having inspection systems (e.g. 116 and 118) immediately upstream and downstream of the fabrication station 106, so that "before" and "after" wafer edge defect data can be compared together to determine whether the process step performed by the fabrication station 106 detrimentally adds new defects to the wafer edge or beneficially repairs preexisting defects. Similarly, the information obtained enables the user to evaluate the performance of groups of fabrication stations (e.g. 108, 110 and 112) by placing inspection systems (e.g. 118 and 120) immediately upstream and downstream of the group of fabrication stations 108, 110 and 112. Such "before" and "after" wafer edge defect data is generally obtained by inspecting the same wafer, or set of wafers, both before and after the selected fabrication station 106 or group of fabrication stations 108-112 and comparing both inspection results.

The information obtained by the inspection systems 116-122 also enables the user to evaluate the effect of making adjustments to one or more of the fabrication stations 102-114. The adjustment-effect evaluation is generally done by inspecting different wafers processed by the same fabrication station 104, 106, 112 or 114 by the inspection station 116, 118, 120 or 122 corresponding thereto both before and after the adjustment is made and comparing average results.

With the information obtained and the evaluations and analyses thereof, the user can adjust the performance of some or all of the fabrication stations 102-114 to increase the efficiency, throughput and yield rate of the over-all fabrication system 100. For instance, the wafer edge defect analyses may reveal to the user that particular adjustments to one or more of the fabrication stations 102-114 can reduce the number of severity of defects added either by the adjusted fabrication station(s) 102-114 or even by another non-adjusted fabrication station 102-114. Additionally, some adjustments to some of the fabrication stations 102-114 may prove to repair some wafer edge defects. Therefore, if it is too costly to adjust one fabrication station 102-114 to reduce added defects, it may be possible to adjust a different fabrication station 102-114 to compensate for the added defects.

Additionally, the wafer edge defect analyses may indicate to the user that certain process steps within one or more of the fabrication stations 102-114 result in certain types of reparable defects, so the user can add one or more fabrication stations to clean, rework or repair the wafers after these process steps. For instance, edge contamination, such as may be caused by contact with a Teflon, or like polymer, edge material of the wafer cassette (e.g. reference 146, FIG. 3, see below) or by another process that contacts or impacts the wafer edge, may be reparable by removing the wafer from the regular process flow and passing the wafer through an edge cleaning or polishing process. After such remedial measures, the wafer may be returned to the regular process flow.

The fabrication system 100 could potentially have enough inspection stations 116-122 to obtain a before-and-after analysis of each process step, or fabrication station 102-114. However, due to space, time and money constraints, it is unlikely that such a case could be achieved for most fabrication systems. Therefore, the selections for the placements of the inspection systems 116-122 depends on which process steps, or fabrication stations 102-114, the user, or designer of the fabrication system 100, considers to be most critical. Additionally, it may be possible for a single inspection system (e.g. 118) to inspect wafers at more than one point in the fabrication system 100, as indicated by the dashed line connected to inspection system 118, thereby allowing the inspection system 118 to perform double-duty. After the most critical process steps, or fabrication stations 102-114, have been analyzed and perhaps adjusted, the inspection systems 116-122 may be moved to other locations in the fabrication system 100 for additional inspection.

The inspection systems 116-122 may remain at the most critical locations within the fabrication system to continue to monitor the performance of some of the fabrication stations 102-114. However, when the fabrication system 100 has proven to be relatively optimized for performance and yield rate, it may be possible to remove some or all of the inspection systems 116-122 from the fabrication system 100 to reduce cost, time and complexity of the over-all fabrication. On the other hand, when the fabrication system 100 exhibits deterioration in its performance, it may be necessary to add inspection systems 116-122 to the fabrication system 100 to diagnose the cause of the deteriorating performance.

The inspection systems 116-122 preferably involve an inspection station 124, a database 126 and a workstation 128, as shown for the exemplary inspection system 116 in FIG. 2. The inspection station 124 is interposed between the preceding fabrication station 104 and the subsequent fabrication station 106 to receive some or all of the wafers (not shown) passing in the process order from the preceding fabrication station 104 to the subsequent fabrication station 106. The database 126 and the workstation 128 may preferably be shared by all of the inspection systems 116-122 (FIG. 1). Additionally, the database 126 and the workstation 128 may be physically located away from the inspection stations 124 and the fabrication stations 102-116, since the database 126 and the workstation 128 do not have to be within a clean-room environment as required for the parts of the fabrication system 100 (FIG. 1) that handle the wafers. The workstation 128 is preferably a conventional general-purpose computer. The database 126 is preferably a conventional computerized mass-storage system.

The inspection station 124 receives the wafers (not shown) and generates "raw" inspection data, preferably digital images, of the wafers. The inspection data is transferred to the database 126 for storage and management. For ease of searching, the stored inspection data for each inspected wafer is correlated with and searchable by an identification (ID) for the wafer and an ID for either the inspection station 124 that took the data, the fabrication station (e.g. 104) preceding the inspection station 124 or the process step performed by the preceding fabrication station 104. The ID for the wafer may include an ID for a "wafer lot" from which the wafer originated and the wafer's ID within the wafer lot.

Using the workstation 128, a user accesses the stored data for one or more wafers and one or more process steps and instructs the workstation 128 to perform various edge defect analyses. For example, the analyses determine whether any defects exist in the edge of one or more of the wafers, whether any defects have been added to the edge of a wafer between two inspection stations 124, whether any defects have been repaired (i.e. "negative adders") on the edge of the wafer by the process step(s) between two inspection stations 124, whether a process step is still causing wafer edge defects even after the process step has been adjusted, etc.

To perform these types of analyses, it is necessary to maintain the inspection data within the database 126 for every wafer for a proper amount of time. In fact, the user may not instruct the workstation 128 to perform these analyses until several minutes or hours after the data has been generated. Therefore, storage of the inspection data is more important for the present invention than it was for the prior art wafer edge defect detection techniques described in the background, which were only concerned with immediate edge defect detection after a given process step, so the inspection data could be immediately deleted thereafter. Thus, the database 126 enables more thorough defect inspection of each wafer and more thorough analysis of the over-all performance of the fabrication system 100 (FIG. 1).

The analyses of the inspection data may involve conventional image-analysis techniques, such as comparing a recorded image to an ideal image to determine any differences, which may indicate various types of anomalies in the recorded image. Thus, the recorded image of the edge of a selected wafer is preferably compared to an image of an ideal wafer edge to generate defect data indicating the locations of possible defects on the edge of the selected wafer.

For a wafer that has been inspected both before and after one or more process steps, "before" and "after" edge defect data can be generated for the wafer and compared together to determine the effect of the intervening process step(s). For example, defect data that indicates more and/or larger defects in the "after" data indicates that the intervening process step(s) added defects to the edge of the wafer. On the other hand, defect data that indicates fewer and/or smaller defects in the "after" data indicates that the intervening process step(s) repaired defects that existed on the edge of the wafer before the intervening process step(s). Rather than comparing the defect data, however, the "before" and "after" recorded images of the edge of the wafer may be directly compared to each other to locate any added or repaired defects.

For different wafers that have been inspected both before and after the same process step, the average performance of the process step, or the fabrication station 102-114 (FIG. 1), can be determined. If the process step needs to be adjusted, then both before-adjustment and after-adjustment inspection data can be generated. Upon comparing before-adjustment and after-adjustment inspection data together, the effect of the adjustment can be determined.

Three exemplary embodiments for the inspection station 124 are shown in FIGS. 3, 4 and 5 with different wafer-handling techniques. Each of the inspection stations 124 has a housing 130. Each of the inspection stations 124 has similar image capturing devices 132 and 134, such as scanning electron microscopes, digital cameras, and the like, for capturing images of the edge of an exemplary wafer 136. Two image capturing devices 132 and 134 are shown, but in a particular embodiment, only one such image capturing device 132 or 134 is used. With more than one image capturing device 132 or 134, though, different sets of inspection data can be obtained almost simultaneously using different imaging techniques that may highlight different types of edge defects.

The wafer 136 sits on a chuck 138. The chuck 138 rotates the wafer 136 while the image capturing devices 132 and 134 scan the edge of the wafer 136 and capture images thereof. The image capturing devices 132 and 134 send image data through connection lines 140 and 142, respectively, to the database 126 (FIG. 2).

The inspection stations 124 include at least one robot arm 144 for moving each wafer 136 onto and off of the chuck 138. The FIG. 3 inspection station 124 further includes a conventional removable wafer cassette (or conventional wafer indexer) 146 which contains each wafer 136 that is to be inspected or has been inspected. The robot arm 144 moves each wafer 136 to be inspected from the wafer cassette 146 to the chuck 138 for inspection and back to the wafer cassette 146 after inspection.

The FIG. 4 inspection station 124 includes two removable wafer cassettes (or wafer indexers) 148 and 150. One of the wafer cassettes 148 contains each wafer 136 that is coming into the inspection station 124 to be inspected. The other wafer cassette 150 contains each wafer 136 that has been inspected and is leaving the inspection station 124. Thus, the robot arm 144 moves each incoming wafer 136 from the incoming wafer cassette 148 to the chuck 138 to be inspected and moves each inspected wafer 134 to the outgoing wafer cassette 150.

The FIG. 5 inspection station 124 includes a second robot arm 152. The first robot arm 144 moves each incoming wafer 136 from the incoming wafer cassette 148 to the chuck 138 to be inspected. The second robot arm 152 then moves each inspected wafer 136 from the chuck 138 to the outgoing wafer cassette 150.

Each configuration for the inspection station 124 (FIGS. 3, 4 and 5) has a different speed or throughput capability and a tradeoff in space and cost requirements. Therefore, the selection of the configuration for the inspection station 124 depends on the cost/benefit for the desired wafer throughput.

Each wafer 136, as shown in FIG. 6, includes an orientation location point, such as a notch 154, etc. The inspection station 124 (FIGS. 2-5) locates the notch 154 to orient the wafer 136 on the chuck 138 (FIGS. 3-5) and then scans the edge 156 of the wafer 136 either for a full 360° from the notch 154 back to the notch 154 or for some smaller inspection area, such as a 90° or 180° section or some other range depending on whatever portion of the wafer 136 needs to be inspected. The image capturing device 132 and 134 then captures an image of the desired inspection area and transfers the image to the database 126 (FIG. 2).

A typical wafer 136, as shown in FIG. 7, has an edge, or bevel, 158 with a slight convex curvature. The top 160 and bottom 162 (at approximately 0° and 180°, respectively, of the curvature) of the edge 158 have a smaller radius of curvature than does the middle of the edge 158. The primary area of interest for edge inspection extends from a point on the top surface 164 of the wafer 136 slightly interior of the top 160 of the edge 158 to a point slightly exterior of the bottom 162 of the edge 158, or any portion thereof, as indicated by the arrow A. The image capturing device 134, therefore, may have a field of view that incorporates the entire desired inspection area, or may be moved relative to the edge 158 along the arrow A to any angle at which a desired portion of the edge 158 is to be scanned.

The image capturing device 134 automatically scans the desired portion of the edge 158 of the wafer 136 and captures an image thereof. The image capturing device 134 preferably does this procedure according to a "recipe" that specifies various parameters that affect the image that will be captured. For instance, the recipe may include values for: the angle of the image capturing device 134 relative to the edge 158 of the wafer 136 along arrow A, the magnification of the image capturing device 134, the focus of the image capturing device 134 (given the curvature of the edge 158, every point in the area of interest may not be in focus at the same time), brightness of one or more illumination sources 166 that illuminate the edge 158 of the wafer 136 in the case that the image capturing device 134 is an optical device, portion of the edge 158 of the wafer 136 to be scanned (e.g. portion of arrow A), the rotational speed of the wafer 136 or the chuck 138 (FIGS. 3-5), a gain setting on a photomultiplier sensor, contrast setting, the accelerating voltage for an electron beam and probe current in the event that the image capturing device 134 is a scanning electron microscope, the angular location of the desired sample area, and threshold values for determining a defect, among other possible parameters for the inspection recipe. The recipe, as well as the captured image, may be stored in the database 126 (FIG. 2) for each wafer 136 scanned, so the image analysis can take into account any of these parameters. Additionally, when comparing two different images, it may be preferable for the recipe to have been the same when capturing both images.

The results of defect analyses for two exemplary inspection procedures are shown graphically in FIG. 8. The first inspection procedure and analysis resulted in defect data 168 for a full 360° inspection area around the edge 158 (FIGS. 6 and 7) of a wafer 136 (FIGS. 3-7) and for a full primary area of interest, as described above with reference to FIG. 7. The second inspection procedure and analysis resulted in defect data 170 for the same area.

The defect data 168 indicated that defects 172-180 were detected. The defect data 170, on the other hand, indicated that defects 172-178, 182 and 184 were detected. Since some of the detected defects 172-178 were the same for both defect data 168 and 170, it is apparent that, for this example, the two inspection procedures were performed on the same wafer 136 (FIGS. 3-7) after different process steps. By effectively subtracting defect data 168 from defect data 170, the added defects 182 and 184 are exposed, as shown by added defect data 186. Thus, defects 182 and 184 were apparently added to the wafer 136 by the intervening process step(s). On the other hand, by effectively subtracting defect data 170 from defect data 168, the repaired defects 180 are exposed, as shown by repaired defect data 188. Thus, defects 180 were apparently repaired on the wafer 136 by the intervening process step(s).

It is apparent from the previous description that the present invention enables a robust wafer edge defect inspection system. The inspection has the advantage of being automated, so control is achieved simply by adjusting the inspection recipe. Additionally, a very detailed defect analysis can be performed to determine the effect of selected process steps on the condition of the edges of the wafers, so the wafers can be rerouted for repair or the process steps can be adjusted for improved performance. In this manner, the yield rate of the fabrication system 100 (FIG. 1) is improved. Furthermore, the inspection information is stored and readily accessible for any desired analysis at any time on any inspected wafer(s). Thus, the user can perform a detailed analysis on many parts of the fabrication system 100 after the fabrication system 100 has been in operation for any length of time in order to ensure proper functioning of the fabrication system 100 or debugging of potential problems that may arise upon initial assembly of the fabrication system 100 or at any other time.

Presently preferred embodiments of the present invention and many of its improvements have been described with a degree of particularity. This description is of preferred examples of implementing the invention, and is not necessarily intended to limit the scope of the invention. The scope of the invention is defined by the following claims.

The invention claimed is:

1. A method of inspecting a semiconductor wafer for defects using captured image analysis comprising:
    positioning the wafer with an edge thereof relative to an image capturing device;
    positioning the image capturing device at a desired angle relative to the edge of the wafer;
    rotating the wafer;
    scanning the edge of the rotating wafer with the image capturing device;
    recording an image of a desired portion of the edge of the scanned wafer from the image capturing device into a database;
    instructing a computer to analyze the recorded images of the scanned wafer;

identifying any defects in the analyzed recorded images; and upon identifying any defects, recording defect information related to each defect;

wherein:

the scanning step further comprises:

scanning the edge of the wafer from a region interior of a top of the edge to a region exterior of a bottom of the edge.

2. A method of inspecting a semiconductor wafer for defects using captured image analysis comprising:

after a first process step:

positioning the wafer with an edge thereof relative to an image capturing device;

rotating the wafer;

scanning the edge of the rotating wafer with the image capturing device;

recording an image of the scanned wafer from the image capturing device into a database;

instructing a computer to analyze the recorded images of the scanned wafer;

identifying any defects in the analyzed recorded images; and upon identifying any defects, recording defect information related to each defect;

after a second process step, repeating the aforementioned steps;

comparing the defect information recorded after the first process step to the defect information recorded after the second process step; and identifying any new defects as added defects due to the second process step.

3. A method of inspecting a semiconductor wafer for defects using captured image analysis comprising:

after a first process step:

positioning the wafer with an edge thereof relative to an image capturing device;

rotating the wafer;

scanning the edge of the rotating wafer with the image capturing device;

recording an image of the scanned wafer from the image capturing device into a database;

instructing a computer to analyze the recorded images of the scanned wafer, identifying any defects in the analyzed recorded images; and upon identifying any defects, recording defect information related to each defect;

after a second process step, repeating the aforementioned steps;

comparing the defect information recorded after the first process step to the defect information recorded after the second process step;

determining whether any defects identified after the first process step have been reduced after the second process step; and identifying any such reduced defects as repaired defects.

4. A method of inspecting an edge of a semiconductor wafer for defects during fabrication of integrated circuit components on the semiconductor wafer within a fabrication system that includes a plurality of fabrication stations arranged in a processing order and within which a variety of process steps are performed on a plurality of wafers, comprising:

providing a plurality of inspection stations within the fabrication system corresponding to selected ones of the fabrication stations, each inspection station being located in a subsequent processing order to a corresponding one of the selected fabrication stations;

processing a wafer in a first fabrication station;

automatically inspecting an edge of the wafer in a first inspection station;

automatically recording a first set of defects in the edge of the wafer; processing the wafer in a second fabrication station;

automatically inspecting the edge of the wafer in a second inspection station;

automatically recording a second set of defects in the edge of the wafer; and determining a difference between the first and second sets of defects.

5. A method as defined in claim 4 further comprising:

identifying process-induced edge defects from the determined difference between the first and second sets of defects.

6. A method of inspecting an edge of semiconductor wafers for defects during fabrication of integrated circuit components on the semiconductor wafers within a fabrication system that includes a plurality of fabrication stations arranged in a processing order and within which a variety of process steps are performed on a plurality of wafers, comprising:

providing a plurality of inspection stations within the fabrication system corresponding to selected ones of the fabrication stations, each inspection station being located in a subsequent processing order to a corresponding one of the selected fabrication stations;

processing the wafers in the fabrication stations;

inspecting the edge of the wafers in the inspection stations;

upon inspecting each wafer, recording an image of the edge of the wafer;

correlating each recorded image with the wafer from which it was taken and the process step after which it was taken;

selecting two recorded images from among a plurality of the recorded images by specifying the wafer from which both images were taken and the two process steps after which each selected image was taken;

determining any defects that were present on the edge of the specified wafer at times that the two selected recorded images were taken of the edge of the specified wafer by analyzing the two selected recorded images; and determining whether any defects were added to the edge of the specified wafer between the times that the two selected recorded images were taken by comparing the determined defects from the analyzing of the two selected recorded images.

7. A wafer edge defect inspection system comprising:

an image capturing device next to which a wafer can be positioned, the image capturing device being oriented to view at least a portion of an edge of the wafer, the image capturing device automatically generating an image of the edge of the wafer;

a database connected to the image capturing device to receive the generated image of the edge of the wafer, the database automatically storing the received image for subsequent analysis; and a computer connected to the database to retrieve the stored image upon instruction from a user to perform image analysis to locate any defects in the edge of the wafer;

wherein the image capturing device is a first image capturing device, the image generated thereby is a first image and the wafer edge defect inspection system is incorporated into a fabrication system having a plurality of fabrication stations for processing the wafer and forming integrated circuit components thereon, further comprising:

a second image capturing device next to which the wafer can be positioned, the second image capturing device being oriented to view at least the portion of the edge of the wafer, the second image capturing device automatically generating a second image of the edge of the wafer and being connected to the database to supply the second image to the database;

and wherein:

the database automatically stores the second image for subsequent analysis by the computer;

the first image capturing device is incorporated into the fabrication system to receive the wafer after a first fabrication station performs a first process step on the wafer and the first image capturing device generates the first image of the edge of the wafer after the first process step;

the second image capturing device is incorporated into the fabrication system to receive the wafer after a second fabrication station performs a second process step on the-wafer and the second image capturing device generates the second image of the edge of the wafer after the second process step; and the computer retrieves the stored first and second images upon instruction from the user to compare and analyze the first and second images together.

8. A wafer edge defect inspection system as defined in claim 7, wherein:

the computer compares and analyzes the first and second images together upon instruction from the user to determine whether any defects have been added to the edge of the wafer between times that the first and second images thereof are generated.

9. A wafer edge defect inspection system as defined in claim 7, wherein:

the computer compares and analyzes the first and second images together upon instruction from the user to determine whether any defects have been repaired on the edge of the wafer between times that the first and second images thereof are generated.

10. A wafer edge defect inspection system as defined in claim 7 incorporated into a fabrication system having a plurality of fabrication stations within which the wafer is subjected to process steps to form integrated circuit components thereon, and wherein:

at least a portion of the located defects are caused by at least one of the process steps to which the wafer is subjected before the image capturing device automatically generates the image of the edge of the wafer.

* * * * *